Feb. 25, 1969 P. ECKE Plant Pat. 2,865
POINSETTIA PLANT
Filed Aug. 22, 1967
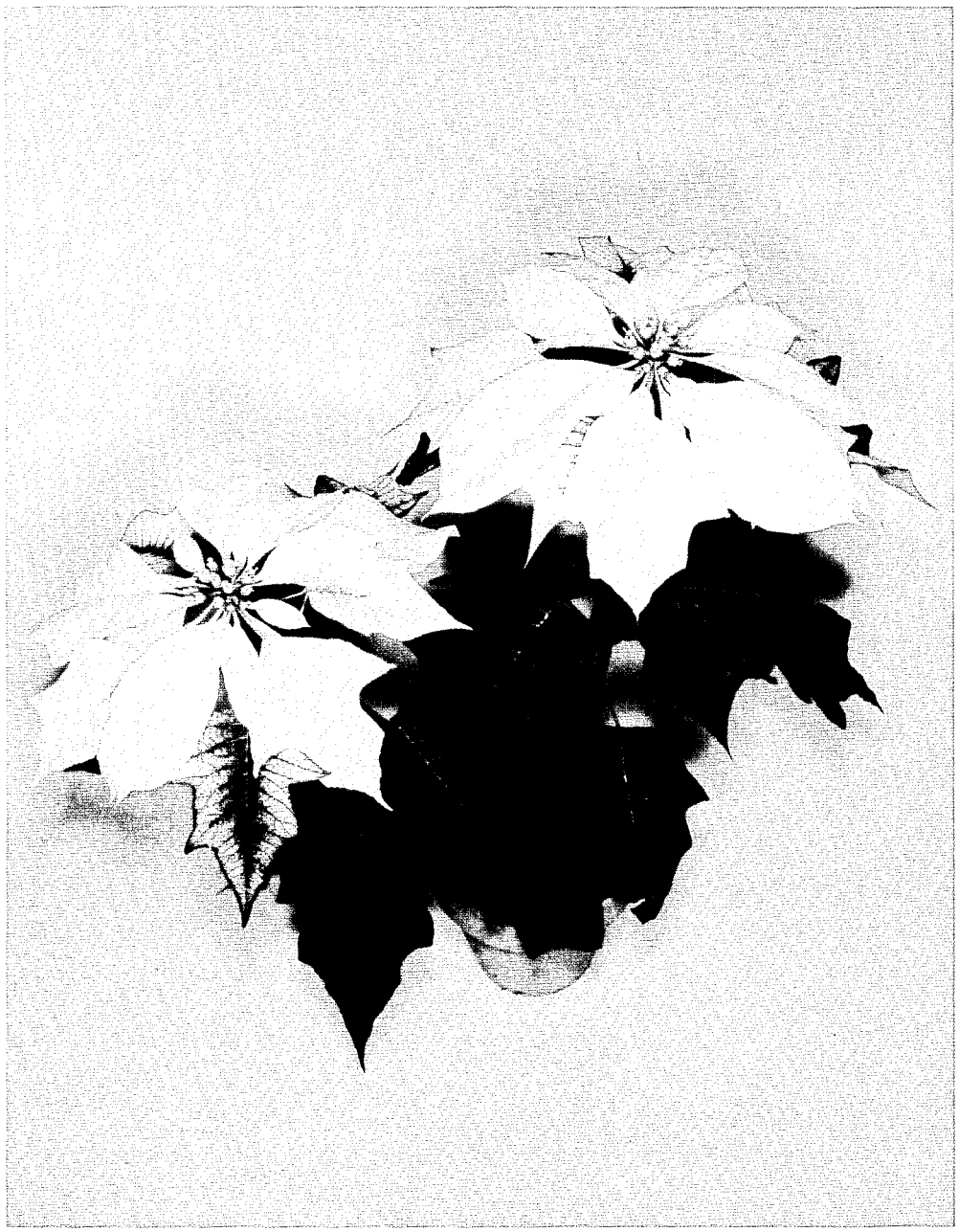
Inventor.
Paul Ecke
By: Robb & Robb
Attorneys.

United States Patent Office

Plant Pat. 2,865
Patented Feb. 25, 1969

2,865
POINSETTIA PLANT

Paul Ecke, P.O. Box 488, Encinitas, Calif. 92024

Filed Aug. 22, 1967, Ser. No. 662,556
U.S. Cl. Plt.—86 1 Claim
Int. Cl. A01h 5/02

The present invention relates to a new and distinct variety of poinsettia plant (botanically known as *Euphorbia pulcherrima*), which was originated by me by crossing an unnamed and unpatented red poinsettia seedling derived from a cross of the variety known as "Paul Mikkelsen" (Plant Patent No. 2,328) × the variety known as "Ecke's White" (unpatented), recrossed with the variety "Ecke's White" aforesaid, the former unnamed variety being the seed parent, and the variety "Ecke's White" being the pollen parent.

The primary objectives of this breeding were to produce a new and improved poinsettia variety having a plant habit which, in general, is more attractive than other white varieties heretofore known in commerce, which has stiff stems that do not require staking, and which retains its foliage and bracts for an unusually long period of time after reaching maturity. These objectives were fully achieved, along with other desirable improvements, as evidenced by the following unique combination of characteristics which are outstanding in the new variety and which distinguish it from its parents, as well as from all other varieties of which I am aware:

(1) A very vigorous, tough and durable plant habit, with the plant being of medium height and having the ability to grow well as a multiple stem and multiple bloom plant;

(2) An extensive root system;

(3) Stiff stems which do not require staking;

(4) Wide bracts of a distinctive shape and arrangement that give the plant an unusually full and complete appearance;

(5) Unusually prolonged retention of the bracts, foliage and inflorescenses after reaching maturity;

(6) An early blooming habit, but having the ability to be satisfactorily brought into bloom and to full maturity in every month of the year, including those months that are ordinarily considered as out-of-season, through the exercise of proper greenhouse cultural techniques;

(7) A distinctive, attractive and graceful contour of the bracts;

(8) A compact inflorescense form which creates an attractive crowned effect in each bloom;

(9) A distinctive and attractive general color tonality of the bracts corresponding to a lively creamy white or ivory color; and

(10) Excellent keeping qualities and consequent suitability for home decoration.

Asexual reproduction of my new variety by vegetative cuttings propagated under mist at Encinitas, Calif., shows that the foregoing characteristics and distinctions come true to form and are established and transmitted through succeeding propagations.

The accompanying drawing shows a typical specimen plant of my new poinsettia variety as depicted in color as nearly true as it is reasonably possible to make the same in a color illustration of this character.

The following is a detailed description of my new poisettia variety, with color terminology in accordance with Wilson's Horticultural Colour Chart (hereinafter abbreviated as (W)) and Koster's Color Guide (hereinafter abbreviated as (K)), except where general color terms of ordinary dictionary significance are obvious, as based on specimens grown at Encinitas, Calif., under regular commercial greenhouse practices:

Parentage: Seedling.

*Seed parent.*—An unnamed red seedling of "Paul Mikkelsen" × "Ecke's White."

*Pollen Parent.*—"Ecke's White."

Propagation: Holds its distinguishing characteristics through succeeding propagations by vegetative cuttings.

Form: Medium tall; upright; graceful contour.

Habit of growth: Vigorous.

Rooting habit: Fast (from 12 to 15 days under mist); vigorous; extensive; uniform.

Blooming habit: Approximately 8 to 9 weeks after start of short days.

Blooming season: Naturally in December, but has excellent suitability for forcing in every month of the year by appropriate greenhouse culture practices.

Foliage: Alternate; borne horizontally on stems; persistent; normal abundance.

*Size.*—Medium; from about 3 inches to 6 inches long; from about 2½ inches to 5 inches wide.

*Shape.*—Mostly deeply serrated; wide at base and tapering to long point at tip.

*Texture.*—Upper side—medium glossy, with ordinary recessed veins. Under side—dull; with ordinary protruding veins.

*Margin.*—Well defined.

*Color.*—Fresh appearance. New foliage: upper side—near Scheele's Green, Plate 860/1, page 175 (W); under side—near Scheele's Green, Plate 860/2, page 175 (W). Old foliage: upper side—near Spinach Green, Plate 0960, page 187 (W); under side—near Spinach Green, Plate 0960/3, page 187 (W).

Disease resistance: Resistant to rhizoctonia and pythium stem and root rot during propagation and growing period, and resistant to botrytis during blooming period, as determined by comparison with other plants grown under the same cultural conditions at Encinitas, Calif., which were infected with these diseases.

Bracts: Average from 14 to 18 in number; wide; excellent retention; new bracts form and develop as other bracts mature; very long lasting qualities; short pointed when young, and becoming even wider at maturity; bracts curve slightly downward at maturity, giving an attractive and graceful appearance; slightly ruffled; borne on short petioles, with consequent full appearance of bloom; retain their color exceptionally well. Color: upper side—between Creamy White, Plate 2 (K) and Sulphury White, Plate 3 (K); under side—near Creamy White, Plate 2 (K).

Flowers:

*Borne.*—Continuously for several months; many flowers per stem in regular clusters in varying stages of development; borne on strong, short stems; slow development, giving a compact appearance for a greater period of time; conspicuous appearance gives a graceful crown effect to bloom.

*Quantity of bloom.*—Relatively abundant; continuous; flowers gradually drop off after maturity but new ones continue to develop as flower stems continue to grow.

*Buds.*—From small to medium size; borne on light green stems. Color—near Lettuce Green, Plate 74 (K).

Reproductive organs:

*Stamens.*—Abundant; from ⅛ to ¼ inch long. Color—near Creamy White, Plate 2 (K).

*Pollen.*—Color—near Naples Yellow, Plate 403, page 121 (W).

*Styles.*—Color—near Sap Green, Plate 62/3, page 62 (W).

*Ovaries.*—Color—near Lettuce Green, Plate 861/2, page 176 (W).

*Nectar cups.*—Color—near Egyptian Buff, Plate 407, page 122 (W).

General observations: As compared with its unnamed seedling parent, the new variety has creamy white or ivory colored bracts instead of the red colored bracts of this parent; it has a greater number of bracts and they are longer than those of the parent; it has a more attractive branched plant habit and is more vigorous; the bracts are more serrated and have a more graceful and less rigid appearance; and the folage is tapered and more deeply serrated than the generally ovate leaves of this parent which are either entire or only slightly serrated. In comparison with its pollen parent, "Ecke's White," the bracts of the new variety are a more live and pure creamy white or ivory color; the bracts are more serrated and their overall appearance is more graceful and less rigid than those of this parent; the flower centers are smaller, with a more full and compact appearance; the plant is less tall; and the foliage is more tapered and less ovate in form, being wider at the base and narrower at the tip.

I claim:

1. A new and distinct variety of poinsettia plant, substantially as herein shown and described, characterized particularly as to novelty by the unique combination of a very vigorous, tough and durable plant habit, with the plant being of medium height and having the ability to grow well as a multiple stem and multiple bloom plant, an extensive root system, stiff stems which do not require staking, wide bracts of a distinctive shape and arrangement that give the plant an unusually full and complete appearance, unusually prolonged retention of the bracts, foliage and inflorescenses after reaching maturity, an early blooming habit, but having the ability to be satisfactorily brought into bloom and to full maturity in every month of the year, including those months that are ordinarily considered as out-of-season, through the exercise of proper greenhouse cultural techniques, a distinctive, attractive and graceful contour of the bracts, a compact inflorescense form which creates an attractive crowned effect in each bloom, a distinctive and attractive general color tonality of the bracts corresponding to a lively creamy white or ivory color, and excellent keeping qualities and consequent suitability for home decorations.

No references cited.

ROBERT E. BAGWILL, *Primary Examiner.*